(12) United States Patent
Wagner et al.

(10) Patent No.: US 9,686,931 B2
(45) Date of Patent: Jun. 27, 2017

(54) HYBRID ALFALFA VARIETY NAMED HYBRIFORCE-3400

(71) Applicant: Alforex Seeds LLC, Indianapolis, IN (US)

(72) Inventors: Steven G. Wagner, Indianapolis, IN (US); Michael J. Velde, Indianapolis, IN (US)

(73) Assignee: Alforex Seeds LLC, Indianapolis, IN (US)

( * ) Notice: Subject to any disclaimer, the term of this patent is extended or adjusted under 35 U.S.C. 154(b) by 0 days.

(21) Appl. No.: 14/792,707

(22) Filed: Jul. 7, 2015

(65) Prior Publication Data

US 2016/0000031 A1    Jan. 7, 2016

Related U.S. Application Data

(60) Provisional application No. 62/021,360, filed on Jul. 7, 2014.

(51) Int. Cl.
*A01H 5/00* (2006.01)
*C12N 15/82* (2006.01)
*A01H 5/10* (2006.01)
*A01H 1/02* (2006.01)

(52) U.S. Cl.
CPC .................. *A01H 5/10* (2013.01); *A01H 1/02* (2013.01); *C12N 15/8241* (2013.01)

(58) Field of Classification Search
None
See application file for complete search history.

(56) References Cited

U.S. PATENT DOCUMENTS

| | | |
|---|---|---|
| 3,710,511 A | 1/1973 | Patterson |
| 3,861,709 A | 1/1975 | Mulcahy et al. |
| 4,535,060 A | 8/1985 | Comai |
| 4,654,465 A | 3/1987 | Brar et al. |
| 4,727,219 A | 2/1988 | Brar et al. |
| 4,769,061 A | 9/1988 | Comai |
| 4,940,835 A | 7/1990 | Shah et al. |
| 4,971,908 A | 11/1990 | Kishore et al. |
| 4,975,374 A | 12/1990 | Goodman et al. |
| 5,145,783 A | 9/1992 | Kishore et al. |
| 5,188,642 A | 2/1993 | Shah et al. |
| 5,188,960 A | 2/1993 | Payne et al. |
| 5,310,667 A | 5/1994 | Eichholtz et al. |
| 5,312,910 A | 5/1994 | Kishore et al. |
| 5,432,068 A | 7/1995 | Albertsen et al. |
| 5,463,175 A | 10/1995 | Barry et al. |
| 5,489,520 A | 2/1996 | Adams et al. |
| 5,491,288 A | 2/1996 | Chaubet et al. |
| 5,510,471 A | 4/1996 | Lebrun et al. |
| 5,550,318 A | 8/1996 | Adams et al. |
| 5,559,223 A | 9/1996 | Falco et al. |
| 5,561,236 A | 10/1996 | Leemans et al. |
| 5,633,435 A | 5/1997 | Barry et al. |
| 5,633,436 A | 5/1997 | Wandelt |
| 5,633,448 A | 5/1997 | Lebrun et al. |
| 5,646,024 A | 7/1997 | Leemans et al. |
| 5,648,477 A | 7/1997 | Leemans et al. |
| 5,689,052 A | 11/1997 | Brown et al. |
| 5,776,760 A | 7/1998 | Barry et al. |
| 5,804,425 A | 9/1998 | Barry et al. |
| 5,850,016 A | 12/1998 | Jung et al. |
| 5,866,775 A | 2/1999 | Eichholtz et al. |
| 5,874,265 A | 2/1999 | Adams et al. |
| 5,879,903 A | 3/1999 | Strauch et al. |
| 5,880,275 A | 3/1999 | Fischhoff et al. |
| 5,885,801 A | 3/1999 | Rao |
| 5,885,802 A | 3/1999 | Rao |
| 5,891,859 A | 4/1999 | Thomashow et al. |
| 5,892,009 A | 4/1999 | Thomashow et al. |
| 5,912,414 A | 6/1999 | Falco et al. |
| 5,919,675 A | 7/1999 | Adams et al. |
| 5,929,305 A | 7/1999 | Thomashow et al. |
| 5,939,599 A | 8/1999 | Chui et al. |
| 5,965,705 A | 10/1999 | Thomashow et al. |
| 5,969,213 A | 10/1999 | Adams et al. |
| 5,990,389 A | 11/1999 | Rao et al. |
| RE36,449 E | 12/1999 | Lebrun et al. |
| 6,040,497 A | 3/2000 | Spencer et al. |
| 6,063,947 A | 5/2000 | DeBonte et al. |
| 6,084,153 A | 7/2000 | Good et al. |
| 6,107,547 A | 8/2000 | Coruzzi et al. |
| 6,127,600 A | 10/2000 | Beach et al. |
| 6,130,366 A | 10/2000 | Herrera-Estrella et al. |
| 6,177,275 B1 | 1/2001 | Coruzzi et al. |
| 6,177,616 B1 | 1/2001 | Bartsch et al. |
| 6,194,638 B1 | 2/2001 | Dhugga et al. |
| 6,197,561 B1 | 3/2001 | Martino-Catt et al. |
| 6,225,114 B1 | 5/2001 | Eichholtz et al. |
| 6,232,529 B1 | 5/2001 | Singletary et al. |
| 6,248,876 B1 | 6/2001 | Barry et al. |
| RE37,287 E | 7/2001 | Lebrun et al. |
| 6,291,224 B1 | 9/2001 | Martino-Catt et al. |
| 6,307,126 B1 | 10/2001 | Harberd et al. |
| 6,323,392 B1 | 11/2001 | Charne |
| 6,338,961 B1 | 1/2002 | DeRose et al. |
| 6,346,403 B1 | 2/2002 | Rafalski et al. |
| 6,372,965 B1 | 4/2002 | Lightner et al. |
| 6,391,348 B1 | 5/2002 | Stilborn et al. |
| 6,399,859 B1 | 6/2002 | Nichols et al. |
| 6,417,428 B1 | 7/2002 | Thomashow et al. |
| 6,423,886 B1 | 7/2002 | Singletary et al. |
| 6,441,274 B1 | 8/2002 | Cahoon et al. |
| 6,459,019 B1 | 10/2002 | Falco et al. |
| 6,531,648 B1 | 3/2003 | Lanahan et al. |
| 6,566,587 B1 | 5/2003 | Lebrun et al. |
| 6,573,430 B1 | 6/2003 | Bradley et al. |
| 6,652,195 B2 | 11/2003 | Vickars et al. |
| 6,664,445 B1 | 12/2003 | Falco et al. |

(Continued)

*Primary Examiner* — Vinod Kumar
(74) *Attorney, Agent, or Firm* — Ronald S. Maciak; Michael Best & Friedrich LLP

(57) ABSTRACT

Disclosed is an alfalfa seed designated HybriForce-3400 and deposited as ATCC Accession Number PTA-123758. Also disclosed are plants, or parts thereof, grown from the seed of the cultivar, plants having the morphological and physiological characteristics of the HybriForce-3400 cultivar, and methods of using the plant or parts thereof in alfalfa breeding and alfalfa transformation.

23 Claims, 3 Drawing Sheets

(56) References Cited

U.S. PATENT DOCUMENTS

| | | |
|---|---|---|
| 6,664,446 B2 | 12/2003 | Heard et al. |
| 6,706,866 B1 | 3/2004 | Thomashow et al. |
| 6,713,663 B2 | 3/2004 | Weigel et al. |
| 6,717,034 B2 | 4/2004 | Jiang |
| 6,787,683 B1 | 9/2004 | Penna et al. |
| 6,794,560 B2 | 9/2004 | Harberd et al. |
| 6,801,104 B2 | 10/2004 | Zhu et al. |
| 6,803,498 B2 | 10/2004 | Dhugga et al. |
| 6,825,397 B1 | 11/2004 | Lowe et al. |
| 7,968,769 B2 * | 6/2011 | Velde .................. A01H 5/12 435/410 |
| 2003/0009011 A1 | 1/2003 | Shi et al. |
| 2003/0079247 A1 | 4/2003 | Shi et al. |
| 2003/0150014 A1 | 8/2003 | Dhugga et al. |
| 2003/0163838 A1 | 8/2003 | Dhugga et al. |
| 2003/0166197 A1 | 9/2003 | Ecker et al. |
| 2003/0204870 A1 | 10/2003 | Allen et al. |
| 2004/0025203 A1 | 2/2004 | Singletary et al. |
| 2004/0034886 A1 | 2/2004 | Cahoon et al. |
| 2004/0068767 A1 | 4/2004 | Dhugga et al. |
| 2004/0078852 A1 | 4/2004 | Thomashow et al. |
| 2004/0098764 A1 | 5/2004 | Heard et al. |
| 2004/0128719 A1 | 7/2004 | Klee et al. |

* cited by examiner

HYBRID ALFALFA VARIETY NAMED HYBRIFORCE-3400

CROSS-REFERENCE TO RELATED APPLICATIONS

This application claims priority to U.S. Provisional Application No. 62/021,360 filed Jul. 7, 2014, the entire contents of which are incorporated herein by reference.

TECHNICAL FIELD

This present disclosure relates to the field of alfalfa (*Medicago sativa*) breeding, specifically relating to a hybrid alfalfa variety designated HybriForce-3400.

BACKGROUND

Alfalfa (*Medicago sativa*) has often been referred to as the "Queen of Forages" because it is an excellent source of protein and digestible fiber, and because of its wide adaptation. Alfalfa has a high mineral content and contains at least 10 different vitamins and is an important source of vitamin A. Alfalfa improves soil tilth, and, in symbiosis with nitrogen fixing bacteria, is highly effective in converting atmospheric nitrogen to biological nitrogen. Thus, alfalfa is an ideal crop for use in crop rotation to improve soil tilth and replenish nutrients depleted from the soil by other crops such as corn. The environment in which plants are grown for agricultural production continuously offers new obstacles to forage production. Development of stable, high yielding cultivars with superior characteristics is an ongoing goal of alfalfa breeders.

SUMMARY

The present invention is directed to a *Medicago sativa* seed designated as HybriForce-3400. The sample of said seed has been deposited as ATCC Accession Number PTA-123758.

The present invention is directed to a plant, or a part thereof, produced by growing said seed.

The present invention is directed to a pollen from said plant.

The present invention is directed to an ovule from said plant.

The present invention is directed to an alfalfa plant having all the physiological and morphological characteristics of said plant.

The present invention is directed to a tissue culture of regenerable cells from said alfalfa plant, or the part thereof. The regenerable cells may be selected from the group consisting of protoplasts and calli. The regenerable cells may be from a leaf, pollen, ovule, cotyledon, hypocotyl, embryo, root, pod, flower, shoot or stalk.

The present invention is directed to a protoplast produced from said tissue culture. The culture may be a callus culture.

The present invention is directed to an alfalfa plant regenerated from said tissue culture. The alfalfa plant has all of the physiological and morphological characteristics of a plant produced by growing a seed designated HybriForce-3400 and deposited under ATCC Accession No. PTA-123758.

The present invention is directed to a tissue culture of regenerable cells from said alfalfa plant having all the physiological and morphological characteristics of said plant, or the part thereof. The regenerable cells may be selected from the group consisting of protoplasts and calli. The regenerable cells may be from a leaf, pollen, ovule, cotyledon, hypocotyl, embryo, root, pod, flower, shoot or stalk.

The present invention is directed to a protoplast produced from said tissue culture of regenerable cells from said alfalfa plant having all the physiological and morphological characteristics of said plant, or the part thereof. The culture may be a callus culture.

The present invention is directed to an alfalfa plant regenerated from the tissue culture of regenerable cells from said alfalfa plant having all the physiological and morphological characteristics of said plant, or the part thereof. The plant has all of the physiological and morphological characteristics of a plant produced by growing a seed designated HybriForce-3400 and deposited under ATCC Accession No. PTA-123758.

The present invention is directed to a method for producing an alfalfa cultivar HybriForce-3400-derived alfalfa plant. The method comprises (a) crossing HybriForce-3400 plants grown from HybriForce-3400 seed, representative seed of which has been deposited under ATCC Accession No: PTA-123758, with a second alfalfa plant to yield progeny alfalfa seed; and (b) growing the progeny seed to yield an alfalfa cultivar HybriForce-3400-derived alfalfa plant. The method further comprises (c) crossing the alfalfa cultivar HybriForce-3400-derived alfalfa plant of (b) with itself or a third alfalfa plant to yield a second alfalfa HybriForce-3400-derived alfalfa progeny seed; and (d) growing the second alfalfa progeny seed of (c) to yield a second alfalfa cultivar HybriForce-3400-derived alfalfa plant. Steps (c) and (d) are repeated at least one time to generate an additional alfalfa cultivar HybriForce-3400-derived alfalfa plant.

The present invention is directed to a method of introducing a desired trait into alfalfa HybriForce-3400. The method comprises (a) crossing HybriForce-3400 plants grown from HybriForce-3400 seed, representative seed of which has been deposited under ATCC Accession No: PTA-123758, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the HybriForce-3400 plants to produce backcross progeny plants; (d) selecting for backcross progeny plants that have the desired trait and physiological and morphological characteristics of alfalfa variety HybriForce-3400 to produce selected backcross progeny plants; and (e) repeating steps (c) and (d) three or more times in succession to produce selected fourth or higher backcross progeny plants that comprise the desired trait and all the physiological and morphological characteristics of alfalfa variety HybriForce-3400.

The present invention is directed to a plant produced by said method of introducing a desired trait into alfalfa HybriForce-3400. The plant has the desired trait and all of the physiological and all morphological characteristics of alfalfa variety HybriForce-3400.

The present invention is directed to a method for producing an alfalfa plant having an altered agronomic trait. The method includes introducing a polynucleotide into a Hybri- Force-3400 plant grown from HybriForce-3400 seed, representative seed of which has been deposited under ATCC Accession No: PTA-123758. The polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering. The polynucleotide is expressed in the plant.

The present invention is directed to an alfalfa plant produced by said method for producing an alfalfa plant.

DETAILED DESCRIPTION

Figure 1:
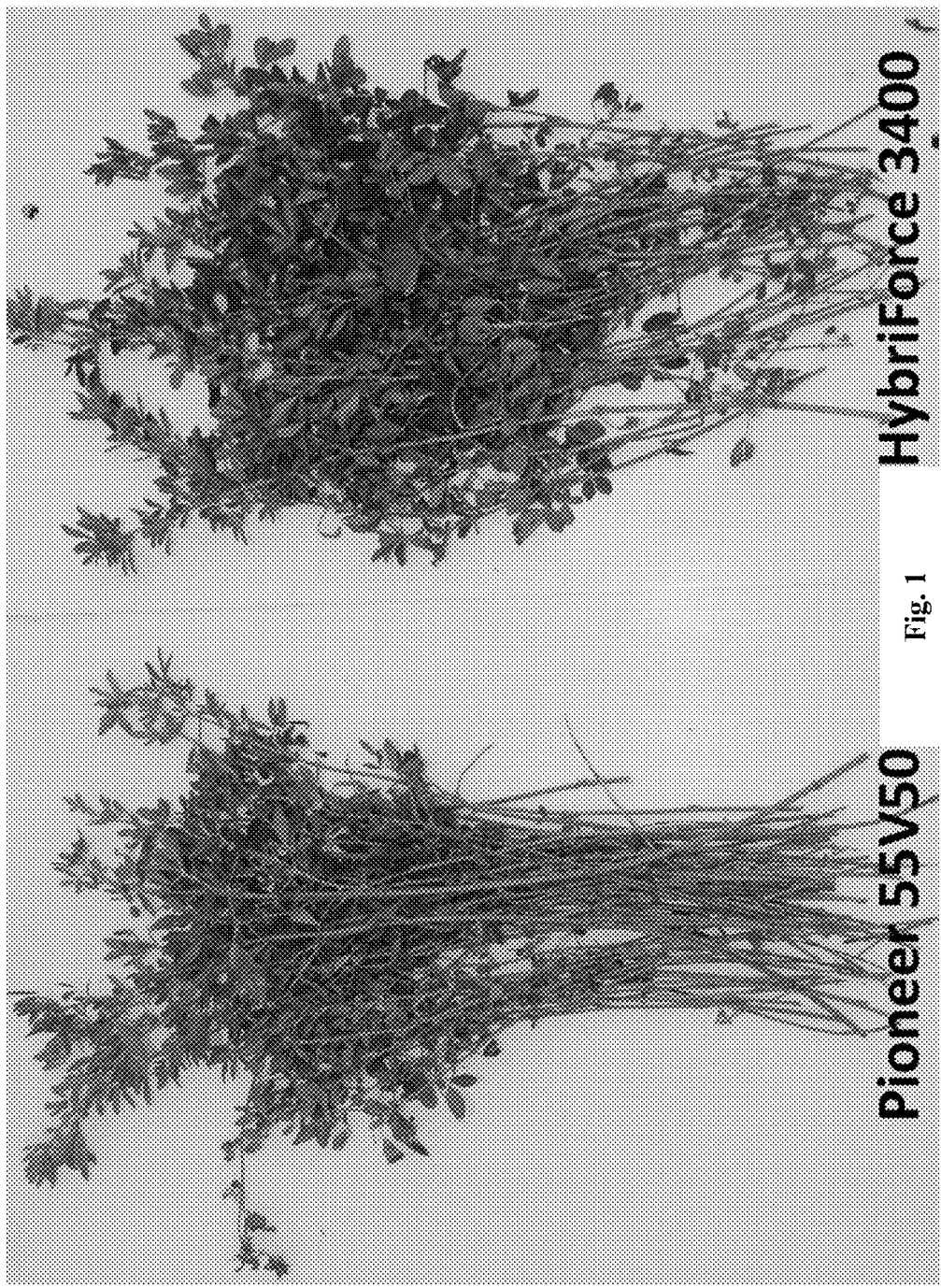
FIG. 1 shows a side by side comparison between Pioneer 55V50 alfalfa and HybriForce-3400 alfalfa.

The present disclosure provides a novel alfalfa variety, designated HybriForce-3400 and processes for making HybriForce-3400. This disclosure relates to seed of alfalfa variety HybriForce-3400, to the plants of alfalfa variety HybriForce-3400, to plant parts of alfalfa variety HybriForce-3400, and to processes for making an alfalfa variety plant that comprise crossing alfalfa variety HybriForce-3400 with another alfalfa plant. This disclosure also relates to processes for making an alfalfa variety plant containing in its genetic material one or more traits introgressed into HybriForce-3400 through backcross conversion and/or transformation, and to the alfalfa seed, plant and plant part produced by said introgression. This invention further relates to alfalfa seed, plant or plant part produced by crossing the alfalfa variety HybriForce-3400 or an introgressed trait conversion of HybriForce-3400 with another alfalfa population. This disclosure also relates to alfalfa populations derived from alfalfa variety HybriForce-3400 to processes for making other alfalfa populations derived from alfalfa variety HybriForce-3400 and to the alfalfa populations and their parts derived by the use of those processes.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

Terms used in the descriptions and tables that follow are defined as follows:

Acid Detergent Fiber ("ADF"). Acid detergent fiber approximates the amount of cellulose fiber and ash present in a feed.

Acid Detergent Lignin ("ADL"). Acid detergent lignin is the lignin in the residue determined following extraction with acid detergent.

Anthracnose. Anthracnose is a serious stem and crown rot disease of alfalfa which can kill individual plants and cause rapid stand decline. Anthracnose is caused by *Colletotrichum trifolii*, a fungus which produces masses of tiny spores on infected stems and crowns. During periods of hot, rainy weather, spores are splashed from infected to healthy plants. Lesions develop on stems, causing stems to wilt and eventually die. The pathogen grows from stem tissue into the plant crown, and causes a crown rot which ultimately kills the plant.

*Aphanomyces* Root Rot. *Aphanomyces* root rot is caused by the fungal-like pathogen *Aphanomyces euteiches* causes death and poor growth of seedling alfalfa in slowly drained fields. It also can be a chronic disease of established plants that may result in significant yield reduction. *Aphanomyces* root rot is similar to and may occur in a complex with *Phytophthora* root rot and *Pythium* damping off, diseases which also occur in wet or slowly drained soils. Plants infected with *Aphanomyces* usually are stunted and chlorotic before they wilt and die, whereas *Phytophthora* and *Pythium* tend to kill seedlings quickly before plants become severely chlorotic.

Bacterial Wilt. The disease is caused by *Clavibacter michiganense* subsp. *insidiosum* (McCulloch) Davis et al.=*Corynebacterium insidiosum* (McCulloch) Jensen. The bacterium survives in plant material in the soil, hay and seed for several years. It can be spread plant to plant via surface water (rain) irrigation and contaminated implement. Bacterial wilt is most common on plants growing in low, poorly drained areas of the field. It is also more common in wet years. Primary infection occurs when bacteria enter roots via wounds. Wounding can be caused by insect or nematode feeding, winter injury of mechanical injury. Once the bacterium enters the plant, symptoms are slow to develop, usually visible in the second or third crop year.

DM. DM is the abbreviation for Dietary Dry Matter and used to calculate yield.

Fall dormancy. Most alfalfa plants go dormant in the fall in preparation for winter. The onset of dormancy is triggered by a combination of day length and temperature and is genotype dependent. Fall dormancy scores measure the dormancy response of alfalfa genotypes by quantifying how early dormancy is triggered. The standard fall dormancy test requires that plants are cut off in early September with plant height measured in mid-October. Early fall dormant types show very little growth after the September clipping, later fall dormant type demonstrate substantial growth. Alfalfa is classified into fall dormancy classes numbered 1 through 11, where dormancy group 1 is very early fall dormant suited for cold climates and dormancy group 11 is very non-dormant and suited for very hot climates in which the plant would grow throughout the winter months.

Flower color. Modern alfalfas are characterized by flower colors: purple, variegated, white, yellow and cream. Some cultivars are heterogeneous for flower color whereby some are predominately purple and variegated.

Forage yield. Forage yield is measured by harvesting herbage for part of or the entire life of the stand.

*Fusarium* Wilt. This disease is caused by *Fusarium oxysporum* f. sp. *Medicagines*. Wilting shoots are the first evidence of the disease. In early stages, the leaves may wilt during the day and regain turgidity at night. Bleaching of the leaves and stems follows, and a reddish tinge often develops in the leaves. Only one side of a plant may be affected at first, and after several months, the entire plant dies. Dark or reddish brown streaks occur in the roots appearing in cross section as small partial or complete rings.

In Vitro True Digestibility ("IVTD"). In Vitro True Digestibility is a measurement of digestibility utilizing actual rumen microorganisms.

Milk Per Acre ("MA") and Milk Per Ton ("MT"). Milk Per Ton is an estimate of the milk production that could be supported by a given forage when fed as part of a total mixed ration. The equation for calculating milk per ton uses Neutral-Detergent Fiber ("NDF") and Acid-Detergent Fiber ("ADF") to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. "Milk Per Acre" is determined by combining milk per ton and dry matter yield per acre. These terms are widely used to estimate the economic value of a forage.

Neutral-Detergent Fiber ("NDF"). Neutral-Detergent Fiber represents the total amount of fiber present in the alfalfa.

Northern Root-Knot Nematode. The northern root-rot nematode, *Meloidogyne hapla*, produces tiny galls on around 550 crop and weed species. They invade root tissue after birth. Females are able to lay up to 1,000 eggs at a time in a large egg mass. They are able to survive harsh winters, and persist in cold climates.

Pea Aphid. The long-legged pea aphid *Acyrthosiphon pisum* (Harris) adult is light to deep green with reddish eyes. It has a body length of 2.0 to 4.0 mm and most adults are wingless. The cornicles (a pair of tailpipe-like structures projecting from the abdomen) of this aphid are characteristically long and slender. The egg is approximately 0.85 mm long; the light green egg turns a shiny black before hatching. The nymph, the immature aphid is smaller than, but similar to, the larger wingless adult. It requires four molts to reach the adult stage. Pea aphids extract sap from the terminal leaves and stem of the host plant. Their feeding can result in deformation, wilting, or death of the host depending upon the infestation level. Plants that survive heavy infestations are short and bunchy with more lightly colored tops than those of healthy plants. Wilted plants appear as brownish spots in the field. Moreover, plants are often coated with shiny honeydew secreted by the aphids, and cast skins may give the leaves and ground a whitish appearance.

Persistence. The ability of the cultivar to last over a minimum of two years. This measurement is documented in the visual percent stand remaining at the time of observation.

*Phytophthora* Root Rot. *Phytophthora* root rot is caused by a soil-borne fungus, *Phytophthora medicaginis*, which is present in most alfalfa field soils. This fungus survives in organic debris and becomes active in wet soil. Water-saturated soils allow production of zoospores which have the capability to "swim" to roots and begin the infection process. Infection usually occurs on small lateral roots. From these initial infection points, the fungus gradually grows into the taproot. A yellow, red, or purple discoloration of leaves is the most characteristic above-ground symptom of *Phytophthora* root rot. Damage is most evident in low or poorly-drained areas of a field.

Relative Forage Quality ("RFQ"). Relative Forage Quality ("RFQ") is a numeric value that estimates the energy content of forage for total digestible nutrients as recommended by the National Research Council. Values are assigned to forages based upon the actual fiber digestibility (NDFd) and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Southern Root-Knot Nematode. The southern root-rot nematode, *Meloidogyne incognita*, is a roundworm that infests at the roots of plants, where it deforms the normal root cells. The roots become gnarled and form galls.

Stem Nematode. The stem nematode, *Ditylenchus dipsaci*, consists of microscopic worms approximately 1.5 mm long. The worms penetrate into plants from either the soil or infested planting material and occasionally from seeds. The female lays 250 eggs during a season and six generations may develop under optimum conditions when the temperature is in the range 15-20° C. As the number of nematodes increase, visual signs begin to occur. Leaves may curl, become yellow or die.

Synthetic variety ("SYN"). SYN variety is developed by intercrossing a number of genotypes with specific favorable characteristics and/or overall general favorable qualities. SYN variety can be developed by using clones, inbreds, open pollinated varieties, and/or individual heterozygous plants.

TA. TA is the abbreviation for Tons per Acre and is used to calculate yield.

Total Digestible Nutrients. Total Digestible Nutrients ("TDN") is an estimate of the energy content of a feedstuff based on its relative proportions of fiber, fat, carbohydrate, crude protein, and ash. Because it is expensive to measure each of these components, TDN is usually estimated from ADF or IVTD. Although still used in some areas as a criteria for evaluating alfalfa hay at auctions, TDN has been shown to overestimate the energy content of low quality forages and thus does not accurately reflect the nutritional value of all forage samples.

*Verticillium* Wilt. *Verticillium* wilt is caused by a fungus, *Verticillium albo-atrum*, which enters the water-conducting cells of the alfalfa plant and restricts the upward movement of water and nutrients. The fungus produces spores within the plant, or on cut stem surfaces following harvesting operations. Spores germinate on the cut surfaces and produce filaments (hyphae) that grow into stems and ultimately into roots. *Verticillium* wilt symptoms usually do not become conspicuous until the third production year. A yellow, V-shaped discoloration at the tip of a leaflet is an early indication of *Verticillium* infection. Eventually, leaflets wilt, turn yellow or pink, and often curl or twist. These abnormally small, twisted leaflets occurring near the top of the stem are the most characteristic symptoms of the disease. Stems are stunted, but frequently remain green and erect (in contrast to the drooping stems caused by anthracnose). Taproots appear healthy and sound, but have a dark ring (the water-conducting tissues) which is evident when the taproot is cut in cross section.

Winter survival. This evaluation is a prediction of the ability of the plant to persist over time.

2. HYBRIFORCE-3400

The present invention includes the seed of hybrid alfalfa variety HybriForce-3400. A deposit of HybriForce-3400 seeds has been made under the Budapest Treaty and in accordance with 37 C.F.R. §§1.801-1.809 on Jan. 25, 2017 with the American Type Culture Collection (ATCC), 10801 University Boulevard, Manassas, Va. 20110. The deposited seed has been granted Accession Number PTA-123758. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-123758 are provided.

By "a plant derived from the seed deposited as Accession Number PTA-123758", it is meant a plant that is grown directly from the seed deposited as Accession Number PTA-123758 or a plant that is obtained indirectly from a plant grown from the seed deposited as Accession Number PTA-123758. Plants obtained indirectly from a plant grown from the seed deposited as Accession Number PTA-123758 may be grown from a vegetative cutting, seed, callus or tissue culture obtained from a plant or plant part grown from the seed deposited as Accession Number PTA-123758 or a clonal plant thereof.

HybriForce-3400 is sold as a five clone 75-95% hybrid alfalfa product consisting of a female, maintainer and restorer clones. Parent clones were selected out of forage yield plots and/or disease nurseries. These parent clones were tested for male sterility, maintaining and restoration ability. The parent clones were also progeny tested for one or more of the following traits: forage yield, stand persistence, forage quality, resistance to bacterial wilt, *Fusarium* wilt, *Phytophthora* root rot, anthracnose (Race 1), *Verticillium* wilt and *Aphanomyces* root rot (Race 1).

The female clone, maintainer clone and restorer clone trace to Dairyland experimental germplasm. Female seed was generated by crossing a cytoplasmic male sterile female clone by a maintainer clone by hand greenhouse crosses in 2006. The female clones were harvested to produce the female Breeder Seed near Sloughhouse, Calif. in 2007-09. Female seed was kept separate each year to produce Breeder seed. Male Breeder seed (Syn. 1) was produced in isolation in 2003 and bulked near Sloughhouse, Calif. The female, maintainer and restorer clones were propagated by vegetative cuttings for Breeder Seed increase.

Female Breeder seed was produced by crossing the cytoplasmic male sterile clone (A) by the maintainer clone (B) in field isolation near Sloughhouse, Calif. in 2007-09. Female seed was kept separate across production years. Male Breeder seed (Syn. 1) was produced in isolation in 2003 and bulked near Sloughhouse, Calif. Male Foundation seed (Syn. 2) was produced from Breeder seed. The 75-95% hybrid seed was produced from crossing female seed by either Syn. 1 or Syn. 2 male seed. Two generations of male seed are recognized. A maximum of three harvest years each is permitted on stands producing Breeder and Foundation seed with five years for Certified seed. Dairyland Research International will maintain sufficient seed for the projected life of the variety.

Alfalfa variety HybriForce-3400 is adapted to the North Central and East Central regions of the U.S. and Canada. This variety has been tested in Wisconsin, Minnesota, Nebraska, and Pennsylvania, and is intended for use in the North Central and East Central regions of the U.S. The HybriForce-3400 plant, or part thereof, or an alfalfa plant having the physiological and morphological characteristics of the HybriForce-3400 plant, may be used as a source of hay, haylage, greenchop and dehydration.

HybriForce-3400 was found to be highly resistant to bacterial wilt (*Clavibacter michiganense*), *Fusarium* wilt (*Fusarium oxysporum*), *Phytophthora* root rot (*Phytophthora megasperma*), *Verticillium* wilt (*Verticillium alboatrum*), anthracnose (*Colletotrichum trifolii*) (Race 1), *Aphanomyces* root rot (Race 1) (*Aphanomyces* euteiches), stem nematode (*Ditylenchus dipsaci*) and northern root-knot nematode (*Meloidogyne hapla*). HybriForce-3400 was found to be resistant to, pea aphid (*Acyrthosipon pisum*), and southern root-knot nematode (*Meloidogyne incognita*). HybriForce-3400 was found to be moderately resistant *Aphanomyces* root rot (Race 2) (*Aphanomyces euteiches*).

HybriForce-3400 is fine stemmed, multifoliate leaf (trifoliate), very drought tolerant, and durable under heavy traffic. HybriForce-3400 has strong winter survival, 33/35 disease rating, moderate resistance to Race 2 *Aphanomyces*, more yield beyond 28-day cut, increased leaf retention, and increased forage quality, and maintains forage quality beyond 28-day cut. HybriForce-3400 is very winter hardy similar to the winter survival 2 check. HybriForce-3400 is a moderately dormant variety similar to the fall dormancy 4 check. Flower color in the Syn. 2 generation is 90% purple, 9% variegated with trace amounts of cream, white and yellow. HybriForce-3400 forage yield performance expresses a 4.4% advantage over HybriForce 2400. HybriForce-3400 has 91.8% wins in 500 University Plot head-to-head comparisons and 11.3% average yield advantage versus all competition in University Plots.

The present invention contemplates using the HybriForce-3400 alfalfa plant, or part thereof, or an alfalfa plant having the physiological and morphological characteristics of the HybriForce-3400 alfalfa plant, as a source of breeding material for developing or producing an alfalfa plant in an alfalfa breeding program using plant breeding techniques. Plant breeding techniques useful in the developing or producing alfalfa plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature.

Methods are provided for introducing or introgressing a desired trait into alfalfa HybriForce-3400. High yield alfalfa plants are inter-mated to produce the next generation of seed. Seed from the first cycle, is re-selected, and inter-mated to produce the next generation of high yield plants. This process of selection and inter-mating is conducted until desired level of yield is achieved. Plants are produced that have the desired trait and all the physiological and morphological characteristics of alfalfa variety HybriForce-3400.

As used herein, the term "plant" includes, but is not limited to, plant cells, plant protoplasts, plant cell tissue cultures from which alfalfa plants can be regenerated, plant calli, plant clumps, and plant cells that are intact in plants or parts thereof "Plant part" includes, but is not limited to, embryos, pollen (pollen grains), ovules, seeds, flowers, pods, leaves, roots, root tips, anthers, and the like.

One may obtain alfalfa plants according to the present invention by directly growing the seed HybriForce-3400 or by any other means. An alfalfa plant having all of the physiological and morphological characteristics of HybriForce-3400 can be obtained by any suitable methods, including, but not limited to, regenerating plants or plant parts from tissue culture or cuttings. The scope of the present invention is not limited by the method by which the plant is obtained.

The present invention contemplates genetic transformation of the HybriForce-3400 alfalfa plants. Polynucleotides may be introduced into a plant cell of alfalfa HybriForce-3400 to produce a transgenic HybriForce-3400 alfalfa plant. At least one, two, three, four, five, six, seven, eight, nine or ten polynucleotides may be introduced. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. The regenerated plants have substantially all the morphological and physiological characterists of the alfalfa variety named HybriForce-3400 that are described in the attached tables.

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters that may be used include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-la promoter, glucocorticoid-inducible promoters, and tetracycline-inducible and tetracycline-repressible promoters.

Polynucleotides may also be provided in a vector. Suitable vectors include plasmids and virus-derived vectors. Vectors known in the art that are suitable for transformation into plants, cloning, and protein expression may be used.

The present invention relates to transformed versions of the claimed alfalfa variety HybriForce-3400 as well as hybrid combinations thereof.

Polynucleotides that may be used include, but are not limited to, those that alter an agronomic trait such as conferring resistance to insects, disease, herbicides, or abiotic stress, or by altering fatty acid metabolism, carbohydrate metabolism, starch metabolism, amino acid metabolism, phosphorus metabolism, antioxidant metabolism, male sterility, site specific DNA integration, plant growth, forage yield and flowering. Examples of such traits are described in U.S. Pat. No. 6,652,195, the entire disclosure of which is herein incorporated by reference.

Polynucleotides that may be introduced include those that confer resistance to insects or disease, including, without limitation, coding sequences for plant disease resistance such as tomato Cf-9 for resistance to *Cladosporium fulvum*, tomato Pto for resistance to *Pseudomonas syringae* pv. Tomato, *Arabidopsis* RSP2 for resistance to *Pseudomonas syringae*, *Bacillus thuringiensis* (bt) protein, insect-specific hormones or pheromones and variants and mimetics, such as an ecdysteroid and juvenile hormones. Examples are described in U.S. Pat. Nos. 5,188,960, 5,689,052, and 5,880, 275, the entire disclosures of which are each herein incorporated by reference. A plant resistant to a disease is one that is more resistant to a pathogen as compared to the wild type plant.

Polynucleotides that may be introduced include those that confer resistance to a herbicide, including, without limitation, coding sequences for mutant ALS and AHAS enzymes, coding sequences for glyphosate resistance imparted by mutant 5-enolpyruvl-3-phosphikimate synthase (EPSP), glyphosate N-acetyltransferase, glyphosate oxido-reductase and aroA; coding sequences for glufosinate resistance (phosphinothricin acetyl transferase (PAT) and *Streptomyces hygroscopicus* phosphinothricin acetyl transferase (bar); pyridinoxy or phenoxy proprionic acids and cycloshexones (ACCase inhibitor-encoding genes); triazine (psbA and gs+ genes); benzonitrile (nitrilase gene); coding sequences for acetohydroxy acid synthase; coding sequences for a chimeric protein of rat cytochrome P4507A1 and yeast NADPH-cytochrome P450 oxidoreductase; coding sequences for glutathione reductase and superoxide dismutase; coding sequences for various phosphotransferases; and coding sequences for modified protoporphyrinogen oxidase (protox). Examples are described in U.S. Pat. Nos. 4,975,374, 5,776,760, 5,463,175, 5,969,213, 5,489,520, 5,550,318, 5,874,265, 5,919,675, 5,561,236, 5,648,477, 5,646,024, 6,566,587, 6,338,961, 6,248,876 B1, 6,040,497, 5,969,213, 5,489,520, 5,550,318, 5,874,265, 5,919,675, 5,561,236, 5,648,477, 5,646,024, 6,177,616, 5,879,903, 5,804,425, 5,633,435, 5,145,783, 4,971,908, 5,312,910, 5,188,642, 4,940,835, 5,866,775, 6,225,114 B1, 6,130,366, 5,310,667, 4,535,060, 4,769,061, 5,633,448, 5,510,471, RE 36,449, RE 37,287, and 5,491,288, the entire disclosures of which are each herein incorporated by reference.

Polynucleotides that may be introduced include those that confer or contribute to an altered trait such as altered fatty acids, include, for example, coding sequences for stearoyl- ACP desaturase, FAD-2, FAD-3, LEC1, AGP, Dek1, Superal1, milps, various Ipa genes such as Ipa1, lpa3, hpt or hggt. Examples are described in U.S. Pat. Nos. 6,063,947, 6,323,392, 6,372,965, 6,423,886, 6,197,561, and 6,825,397, and US Patent Publication Nos. 2003/0079247 and 2003/0204870, the entire disclosures of which are each herein incorporated by reference.

Polynucleotides that may be introduced include those that confer or contribute to an altered trait such as altered phosphorus content, include, for example, coding sequences for a phytase, inositol kinase or for LPA alleles. Examples are described in U.S. Pat. Nos. 6,197,561, 6,291,224, and 6,391,348, and US Patent Publication Nos. 2003/0009011, 2003/0079247, and 2003/0079247, the entire disclosures of which are each herein incorporated by reference.

Polynucleotides that confer or contribute to an altered trait such as altered carbohydrate metabolism, include coding sequences for enzymes of starch and cellulose metabolism, such as thioredoxin, fructosyltransferase, levansucrase, alpha-amylase, invertase, starch branching enzyme, UDP-D-xylose 4-epimerase, cellulose synthases (CesA), UDP-glucose pyrophosphorylase, glycosyl transfersase, and glycosyl hydrolase. Examples are described in U.S. Pat. Nos. 6,531,648, 6,232,529, 6,194,638, 6,803,498, 6,194,638, 6,399,859 and US Patent Publication Nos. 2003/0163838, 2003/0150014, 2004/0068767, and 2004/0025203, the entire disclosures of which are each herein incorporated by reference.

Polynucleotides that may be introduced include those that confer or contribute to an altered trait such as altered antioxidant content or composition, include, for example, coding sequences for a phytl prenyl transferase (ppt), or homogentisate geranyl geranyl transferase (hggt). Examples are described in U.S. Pat. No. 6,787,683, and US Patent Publication No. 2004/0034886, the entire disclosures of which are each herein incorporated by reference.

Polynucleotides that may be introduced include those that confer or contribute to an altered trait such as altered amino acids, include for example, coding sequences for plant amino acid biosynthetic enzymes, coding sequences for plant tryptophan synthase, or coding sequences for methionine metabolic enzymes. Examples are described in U.S. Pat. Nos. 6,127,600, 5,990,389, 5,850,016, 5,885,802, 5,885,801 6,664,445 6,459,019 6,441,274 6,346,403, 5,939,599, 5,912,414, 5,633,436, and 5,559,223, the entire disclosures of which are herein incorporated by reference.

Polynucleotides that may be introduced include those that confer or contribute to an altered trait such as male sterility. For example coding sequences for a deacetylase gene, the use of stamen-specific promoters, barnase and barstar genes may be used. Examples are described in U.S. Pat. Nos. 5,432,068, 4,654,465, 4,727,219, 3,861,709, and 3,710,511, the disclosures of each of which are herein incorporated by reference in their entireties.

Polynucleotides that may be introduced include those that create a site for site specific DNA integration, such as the introduction of FRT sites that may be used in the FLP/FRT system and/or Lox sites that may be used in the Cre/Loxp system.

Polynucleotides that may be introduced include those that alter abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) See for example, U.S. Pat. Nos. 5,892,009, 5,965,705, 5,929,305, 5,891,859, 6,417,428, 6,664,446, 6,706,866, 6,717,034, 6,801,104, 6,084,153, 6,177,275, and 6,107,547, and US Patent Publication Nos. 20040128719, 20030166197, 20040098764, and 20040078852. The disclosures of each of these documents are herein incorporated by reference in their entireties.

Polynucleotides that may be introduced include those that alter plant growth and agronomic traits such as yield, flowering, plant growth and/or plant structure. Examples are described in U.S. Pat. Nos. 6,573,430, 6,713,663 6,794,560, and 6,307,126, the disclosures of each of which are herein incorporated by reference in their entireties.

The present invention has multiple aspects, illustrated by the following non-limiting examples.

3. EXAMPLES

The foregoing may be better understood by reference to the following examples, which are presented for purposes of illustration and are not intended to limit the scope of the invention.

Example 1

Disease Resistance of Cultivar and Cultivar Components

The response of HybriForce-3400 to various diseases was evaluated according to the "Standard Tests to Characterize Alfalfa Cultivars, $3^{rd}$ edition, as amended 2004", approved by the North American Alfalfa Improvement Conference. The resistance or susceptibility of the cultivar to bacterial wilt (*Clavibacter michiganense*), Fusarium wilt (*Fusarium oxysporum*), Phytophthora root rot (*Phytophthora megasperma*), Verticillium wilt (*Verticillium albo-atrum*), stem nematode (*Ditylenchus dipsaci*) and northern root-knot nematode (*Meloidogyne hapla*), anthracnose (*Colletotrichum trifolii*) (Race 1), Aphanomyces root rot (Races 1 and 2) (*Aphanomyces euteiches*), pea aphid (*Acyrthosipon pisum*), and southern root-knot nematode (*Meloidogyne incognita*) was assessed. For each disease tested, appropriate check cultivars, including resistant and susceptible cultivars, were employed as controls. For each type of disease tested, each line of plants was assigned to one of five classes of resistance according to the percentage of resistant plants shown in Table 1. The results are presented in Tables 2 through 12 where the "Unadjusted % R" is the actual raw data summary and "Adjusted % R" is transformed to the standards of the resistant check.

TABLE 1

| Class | % Resistant plants |
|---|---|
| Susceptible | <6 |
| Low resistant | 6-14 |
| Moderately resistant | 15-30 |
| Resistant | 31-50 |
| Highly resistant | >50 |

TABLE 2

Resistance to anthracnose (Race 1) disease (*Colletotrichum trifolii*)*

| | Variety | Resistance Class | Year Tested | Syn Gen | Unadjusted % R | Adjusted % R |
|---|---|---|---|---|---|---|
| | HybriForce-3400 | HR | 2009 | F1 | 51 | 55 |
| 1. | Saranac AR | R | | | 42 | 45 |

TABLE 2-continued

Resistance to anthracnose (Race 1) disease (*Colletotrichum trifolii*)*

| | Variety | Resistance Class | Year Tested | Syn Gen | Unadjusted % R | Adjusted % R |
|---|---|---|---|---|---|---|
| 2. | Saranac | S | | | 4 | 4 |
| | Test Mean: | | | | 53 | 57 |
| | L.S.D. (.05%) | | | | 27 | |
| | C.V. (%) | | | | 31 | |

*Greenhouse Test conducted by Dairyland Seed at Clinton, WI.

TABLE 3

Resistance to *Aphanomyces* Root Rot (Race 1) (*Aphanomyces euteiches*)*

| | Variety | Resistance Class | Year Tested | Syn Gen | Unadjusted % R | Adjusted % R |
|---|---|---|---|---|---|---|
| | HybriForce-3400 | HR | 2009 | F1 | 58 | 78 |
| 1. | WAPH-1 (Race 1) | R | | | 37 | 50 |
| 2. | Saranac (Races 1 & 2) | S | | | 5 | 7 |
| | Test Mean: | | | | 52 | 70 |
| | L.S.D. (.05%) | | | | 23 | |
| | C.V. (%) | | | | 40 | |

*Greenhouse Test conducted by Dairyland Seed at Clinton, WI.

TABLE 4

Resistance to *Aphanomyces* Root Rot (Race 2) (*Aphanomyces euteiches*)*

| | Variety | Resistance Class | Year Tested | Syn Gen | Unadjusted % R | Adjusted % R |
|---|---|---|---|---|---|---|
| | HybriForce-3400 | MR | 2009 | F1 | 18 | 20 |
| 1. | WAPH-1 (Race 1) | R | | | 4 | 4 |
| 2. | WAPH-5 (Race 2) | R | | | 45 | 50 |
| 3. | Saranac (Races 1 & 2) | S | | | 5 | 5 |
| | Test Mean: | | | | 28 | 31 |
| | L.S.D. (.05%) | | | | 20 | |
| | C.V. (%) | | | | 25 | |

*Greenhouse Test conducted by Dairyland Seed at Clinton, WI.

TABLE 5

Resistance to Bacterial Wilt Disease (*Clavibacter michiganense*)*

| | Variety | Resistance Class | Year Tested | Syn Gen | Unadjusted % R | Adjusted % R |
|---|---|---|---|---|---|---|
| | HybriForce-3400 | HR | 2009 | F1 | 64 | 58 |
| 1. | Vernal | R | | | 46 | 42 |
| 2. | Narragansett | S | | | 5 | 5 |
| | Test Mean: | | | | 62 | 57 |
| | L.S.D. (.05%) | | | | 16 | |
| | C.V. (%) | | | | 18 | |

*Field Test conducted by Dairyland Seed at Clinton, WI.

TABLE 6

Resistance to *Fusarium* Wilt Disease (*Fusarium oxysporum*)*

| | Variety | Resistance Class | Year Tested | Syn Gen | Unadjusted % R | Adjusted % R |
|---|---|---|---|---|---|---|
| | HybriForce-3400 | HR | 2009 | F1 | 76 | 82 |
| 1. | Agate Field | HR | | | 50 | 54 |
| | Test Mean: | | | | 73 | 79 |
| | L.S.D. (.05%) | | | | 19 | |
| | C.V. (%) | | | | 18 | |

*Field Test conducted by Dairyland Seed at Clinton, WI.

TABLE 7

Resistance to *Phytophthora* Root Rot Disease (*Phytophthora medicaginis*)*

| | Variety | Resistance Class | Year Tested | Syn Gen | Unadjusted % R | Adjusted % R |
|---|---|---|---|---|---|---|
| | HybriForce-3400 | HR | 2009 | F1 | 61 | 69 |
| 1. | WAPH-1 (seedling) | HR | | | 48 | 55 |
| 2. | Saranac | S | | | 3 | 3 |
| | Test Mean: | | | | 57 | 65 |
| | L.S.D. (.05%) | | | | 24 | |
| | C.V. (%) | | | | 47 | |

*Seedling Test conducted by Dairyland Seed at Clinton, WI.

TABLE 8

Resistance to *Verticillium* Wilt Disease (*Verticillium albo-atrum*)*

| | Variety | Resistance Class | Year Tested | Syn Gen | Unadjusted % R | Adjusted % R |
|---|---|---|---|---|---|---|
| | HybriForce-3400 | HR | 2010 | F1 | 75 | 71 |
| 1. | Oneida VR | HR | | | 63 | 60 |
| 2. | Saranac | S | | | 5 | 5 |
| | Test Mean: | | | | 59 | 56 |
| | L.S.D. (.05%) | | | | 15 | |
| | C.V. (%) | | | | 18 | |

*Greenhouse Test conducted by Dairyland Seed at Clinton, WI.

TABLE 9

Resistance to Pea Aphid Insect (*Acyrthosipon pisum*)*

| | Variety | Resistance Class | Year Tested | Syn Gen | Unadjusted % R | Adjusted % R |
|---|---|---|---|---|---|---|
| | HybriForce-3400 | R | 2011 | F1 | 39 | 39 |
| 1. | CUF 101 | HR | | | 55 | 55 |
| 2. | Ranger | S | | | 10 | 10 |
| | Test Mean: | | | | 39 | 39 |
| | L.S.D. (.05%) | | | | 27 | |
| | C.V. (%) | | | | 35 | |

*Greenhouse Test conducted by Dairyland Seed at Sloughhouse, CA.

TABLE 10

Resistance to Northern Root-Knot Nematode (*Meloidogyne hapla*)*

| | Variety | Resistance Class | Year Tested | Syn Gen | Unadjusted % R | Adjusted % R |
|---|---|---|---|---|---|---|
| | HybriForce-3400 | HR | 2009 | F1 | 74 | 76 |
| 1. | Nevada Syn XX | HR | | | 88 | 90 |
| 2. | Lahontan | S | | | 10 | 10 |
| | Test Mean: | | | | 68 | 70 |
| | L.S.D. (.05%) | | | | | 13 |
| | C.V. (%) | | | | | 13 |

*Controlled environment - Greenhouse - Test conducted by Dairyland Seed at Clinton, WI.

TABLE 11

Resistance to Southern Root-Knot Nematode (*Meloidogyne incognita*)*

| | Variety | Resistance Class | Year Tested | Syn Gen | Unadjusted % R | Adjusted % R |
|---|---|---|---|---|---|---|
| | HybriForce-3400 | R | 2009 | F1 | 42 | 36 |
| 1. | Moapa 69 | R | | | 59 | 50 |
| 2. | Lahontan | S | | | 5 | 4 |

TABLE 11-continued

Resistance to Southern Root-Knot Nematode (*Meloidogyne incognita*)*

| Variety | Resistance Class | Year Tested | Syn Gen | Unadjusted % R | Adjusted % R |
|---|---|---|---|---|---|
| Test Mean: | | | | 40 | 34 |
| L.S.D. (.05%) | | | | | 17 |
| C.V. (%) | | | | | 29 |

*Controlled environment - Greenhouse - Test conducted by Dairyland Seed at Clinton, WI.

TABLE 12

Resistance to Stem Nematode (*Ditylenchus dipsaci*)*

| | Variety | Resistance Class | Year Tested | Syn Gen | Unadjusted % R | Adjusted % R |
|---|---|---|---|---|---|---|
| | HybriForce-3400 | HR | 2009 | F1 | 79 | 66 |
| 1. | Lahontan | R | | | 48 | 40 |
| 2. | Ranger | S | | | 12 | 10 |
| | Test Mean: | | | | 60 | 50 |
| | L.S.D. (.05%) | | | | | 23 |
| | C.V. (%) | | | | | 23 |

*Controlled environment - Greenhouse - Test conducted by Dairyland Seed at Clinton, WI.

Example 2

Fall Dormancy

Fall dormancy was determined from spaced plantings relative to seven (7) standard check varieties. Tests were conducted by Dairyland Research at Clinton, Wis. HybriForce-3400 is a moderately dormant variety similar to the fall dormancy 4 ("FD4") check. See Tables 13 and 14.

TABLE 13

Fall Dormancy

| | $FDC^1$ | Score or Average Height — Dormancy Score or Average Height | Syn Gen | Date of Last Cut (Mo/Yr) | Date Measured (Mo/Yr) | LSD .05 | CV % |
|---|---|---|---|---|---|---|---|
| HybriForce-3400 | 4 | 9.0 | F1 | 9/2010 | 10/2010 | 2.2 | 5.8 |
| Check Varieties | | | | | | | |
| Maverick | 1.0 | 2.3 | | | | | |
| Vernal | 2.0 | 4.6 | | | | | |
| 5246 | 3.0 | 6.7 | | | | | |
| Legend | 4.0 | 9.0 | | | | | |
| Archer | 5.0 | 12.6 | | | | | |
| ABI 700 | 6.0 | 15.0 | | | | | |
| Doña Ana | 7.0 | 20.0 | | | | | |
| Pierce | 8.0 | | | | | | |
| CUF 101 | 9.0 | | | | | | |
| UC-1887 | 10.0 | | | | | | |
| UC-1465 | 11.0 | | | | | | |

TABLE 14

HybriForce-3400 is most similar to the following fall dormancy class:

| Very Dormant | Dormant | Moderately Dormant | Non-Dormant | Very Non-Dormant |
|---|---|---|---|---|
| FD 1 ( ) | FD 2 ( ) | FD 4 (X) | FD 7 ( ) | FD 9 ( ) |
| | FD 3 ( ) | FD 5 ( ) | FD 8 ( ) | FD 10 ( ) |
| | | FD 6 ( ) | | FD 11 ( ) |

Example 3

Persistence Advantage of HybriForce-3400

Tests conducted at Landisville, Pa. HybriForce-3400 shows increased persistence compared to Vernal and Oneida VR. See Table 15.

TABLE 15

| | | | | | | Persistence % Stand | | | | |
|---|---|---|---|---|---|---|---|---|---|---|
| Test Location | Syn Gen | Date Seeded Mo/Yr | No. of Years Harvested | No. of Harvests | Date of Readings (Mo/Yr) Initial/Final | HybriForce-3400 Initial/Final | Check Varieties Vernal Initial/Final | Oneida VR Initial/Final | LSD .05 | CV % |
| Landisville, PA | F1 | 4/09 | 3 | 15 | 5//09/10/12 | 100/87 | 100/74 | 100/82 | 5.2 | 4.5 |

Example 4

Survival of Over Wintered Plants

Winter survival was determined from spaced plantings relative to standard check varieties. Tests conducted by Dairyland Research at Clinton, Wis. Check varieties were chosen so as to bracket the winter survival data of HybriForce-3400. Data for check varieties in classes 1 through 6 were included. HybriForce-3400 is very winder hardy, with winter survival similar to the very hardy winter survival class 2. See Tables 16 and 17.

TABLE 16

| | | | | Winter Survival Winter Survival Rating | | | | | | | | |
|---|---|---|---|---|---|---|---|---|---|---|---|---|
| Test Location | Syn Gen | Date Planted (Mo/Yr) | Date Measured (Mo/Yr) | HybriForce-3400 | Check Class 1 | 2 | 3 | 4 | 5 | 6 | LSD .05 | CV % |
| Clinton, WI | 1 | 4/2010 | 5/2011 | 1.4 | 1.0 | 1.4 | 2.4 | 3.0 | 3.4 | 5.0 | .3 | 4.6 |
| Clinton, WI | 1 | 4/2011 | 5/2012 | 1.4 | 1.3 | 1.6 | 2.0 | 2.6 | 3.0 | 4.0 | .3 | 5.6 |

Check Class
1 = ZG 9830;
2 = 5262;
3 = WL325HQ;
4 = G-2852;
5 = Archer;
6 = CUF101

TABLE 17

| | | Winter Survival Classes | | | |
|---|---|---|---|---|---|
| 1 { } | 2 {X} | 3 { } | 4 { } | 5 { } | 6 { } |
| Extremely Winterhardy (ZG 9830) | Very Winterhardy (5262) | Winterhardy (WL325HQ) | Moderately Winterhardy (G-2852) | Slightly Winterhardy (Archer) | Non-Winterhardy (CUF 101) |

Example 5

Flower Color

HybriForce-3400 flower color was classified according to the USDA Agriculture Handbook No. 424-A System for Visually Classifying Alfalfa Flower Color. Flower color at full bloom in the Female(F1)+Male(Syn2) generation is 90% purple, 9% variegated with trace amounts of cream, white and yellow. See Table 18.

TABLE 18

| Flower Color | |
|---|---|
| Color | Percent |
| Purple | 90% |
| Variegated | 9% |
| Cream | Trace |
| Yellow | Trace |
| White | Trace |

Example 6

Forage Yield

Forage yields of HybriForce-3400 were measured and are presented in Tables 19 and 20.

TABLE 19

Total Forage Yield (DM in T/A) (Data collected across at various Midwest locations)
Total Yield (DM in T/A)

| Test Location | Date Planted Mo/Yr | Syn Gen | Year Harvested | No. Cuts | HybriForce-3400 | Check 1 Vernal | Check 2 Oneida VR | Check 3 5312 | LSD .05 | CV % |
|---|---|---|---|---|---|---|---|---|---|---|
| Arlington, WI | 4/08 | F1 | 2009 | 4 | 10.30 | 8.52 | 8.54 | 8.61 | .75 | 4.8 |
| | | | 2010 | 4 | 10.36 | 8.26 | 8.51 | 8.8 | .47 | 3.4 |
| | | | 2011 | 4 | 7.4 | 5.24 | 5.76 | 6.12 | .47 | 4.2 |
| Rosemount, MN | 5/08 | F1 | 2009 | 4 | 5.49 | 5.17 | 5.10 | 5.27 | .39 | 5.0 |
| | | | 2010 | 4 | 7.83 | 6.44 | 6.54 | 7.11 | .51 | 4.8 |
| | | | 2011 | 4 | 5.46 | 4.85 | 4.91 | 5.07 | .27 | 3.45 |
| Landisville, PA | 4/09 | F1 | 2010 | 5 | 10.80 | 7.78 | 9.38 | 8.72 | 1.71 | 13 |
| | | | 2011 | 5 | 9.09 | 6.6 | 7.89 | 7.94 | 1.48 | 13.03 |
| | | | 2012 | 5 | 6.8 | 4.83 | 5.9 | 5.75 | 1.78 | 20.8 |
| Havelock, NE | 4/09 | F1 | 2010 | 5 | 8.44 | 6.1 | | | .98 | 20.7 |
| | | | 2011 | 5 | 8.41 | 5.77 | | | .99 | 17.71 |

TABLE 20

Mean Annual Yield

| | | | Tons DM/Acre | | | |
|---|---|---|---|---|---|---|
| Variety names | # of Years Harvested | Total # of Harvests | HybriForce-3400 | Vernal | Oneida VR | 5312 |
| HybriForce-3400 | 11 | 49 | 8.22 | | | |
| Check 1 Vernal | 11 | 49 | 8.22 | 6.32 | | |
| Check 2 Oneida VR | 9 | 39 | 8.17 | | 6.95 | |
| Check 3 5312 | 9 | 39 | 8.17 | | | 7.04 |

Figure 2:
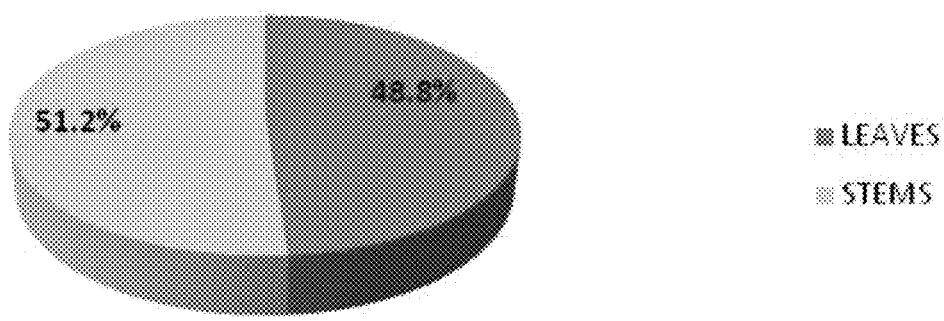
FIG. 2 shows the leaf/stem ratio of HybriForce-3400 compared to Pioneer 55V50.
Figure 2:
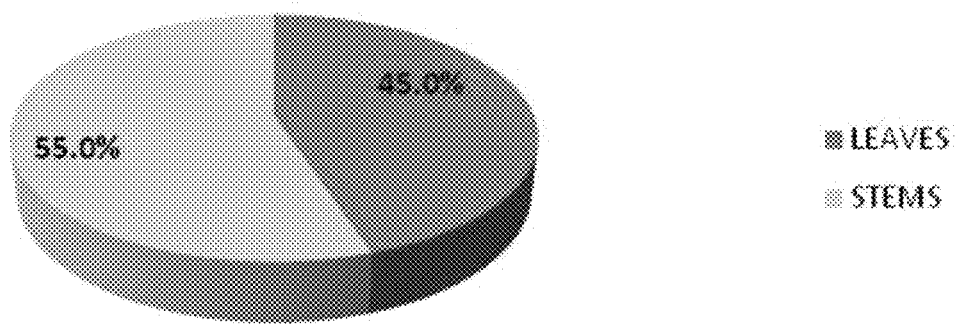

HybriForce-3400 was compared to Pioneer 55V50 (see FIGS. 1 and 2). HybriForce-3400 had 76 more pounds of leaves in 1 ton of hay compared to Pioneer 55V50, which had 76 more pounds of stems in 1 ton of hay (FIG. 2).

Example 7

Leaf/Stem Ratio

Leaf/stem ratios were measured on 9 varieties×2 regimes×2 cuttings in Clinton, Wis. 2 cuttings showed a hint of statistical significant. See Table 21.

TABLE 21

Leaf/Stem Ratio

| Variety | N | % Leaf Actual |
|---|---|---|
| WL354HQ | 4 | 51.8 |
| HF2400 | 4 | 51.0 |
| AMERISTAND407TQ | 4 | 50.3 |
| HF3400 | 4 | 48.8 |

TABLE 21-continued

Leaf/Stem Ratio

| Variety | N | % Leaf Actual |
|---|---|---|
| HF3400QR | 4 | 48.5 |
| CONSISTENCY4.10RR | 4 | 48.5 |
| REBOUND6.0 | 4 | 47.5 |
| 6422Q | 4 | 47.5 |
| 55V50 | 4 | 45.0 |
| MEAN | | 48.8 |
| LSD | | NS |
| CV % | | 7.9% |
| P-Value | | 0.376 |

Example 8

Forage Quality

Figure 3:
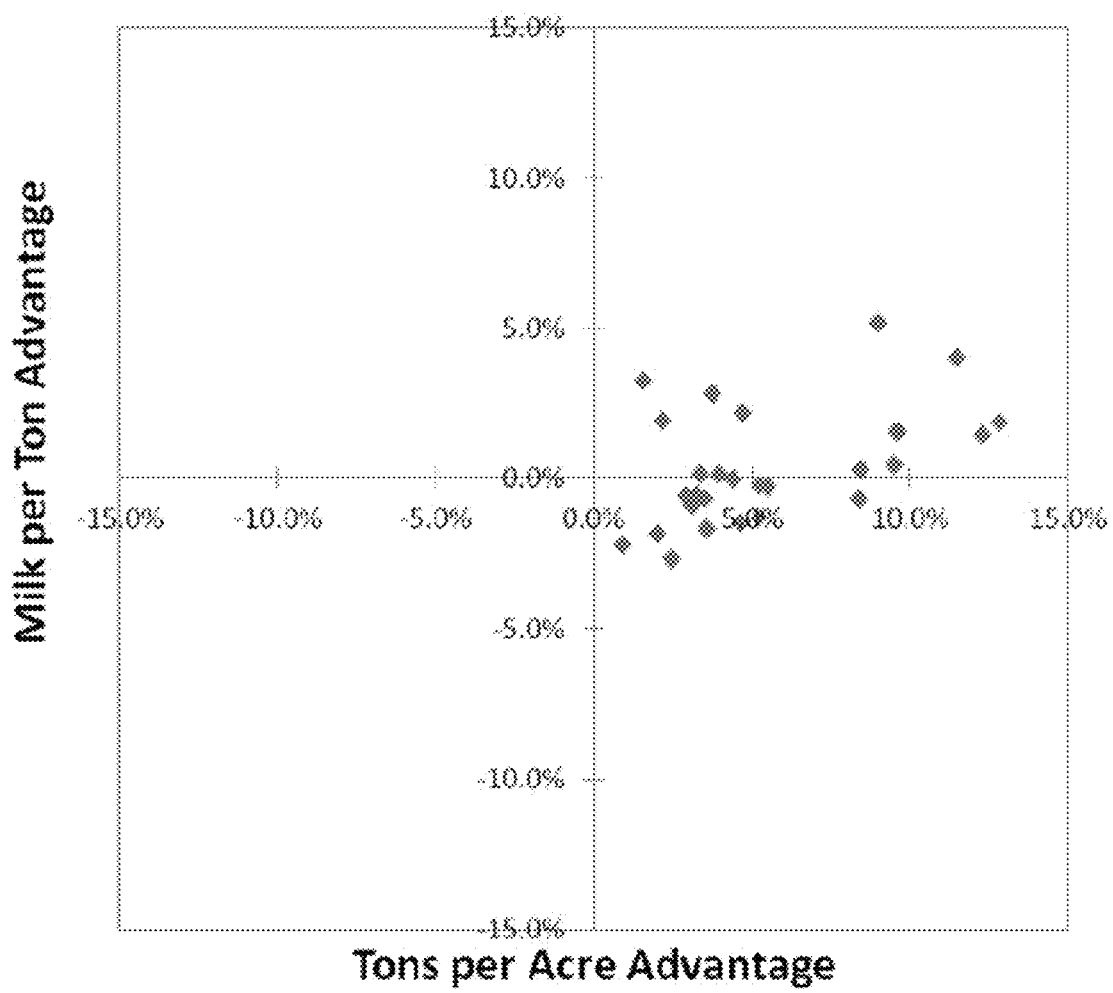
FIG. 3 shows the HybriForce-3400 head-to-head advantage plotted as milk per ton advantage versus tons per acre advantage.

The forage quality was measured with a 3 cut average×2 reps and sorted by RFQ. See Tables 22 and 23 and FIG. 3. Table 23 shows the over the years head-to-head summary sorted by tons/acre advantage.

TABLE 22

| VARIETY | N | TA | RFQ | ADL | MT | MA |
|---|---|---|---|---|---|---|
| HF3400QR | 6 | 1.92 | 178 | 6.41 | 2958 | 5638 |
| 53VR03RR | 6 | 1.83 | 177 | 6.13 | 2973 | 5414 |
| HF3400 | 6 | 1.93 | 175 | 6.67 | 2950 | 5606 |
| MAGNUM7 | 6 | 1.92 | 172 | 6.30 | 2952 | 5619 |

TABLE 22-continued

| VARIETY | N | TA | RFQ | ADL | MT | MA |
|---|---|---|---|---|---|---|
| LIBERATORRR | 6 | 1.90 | 172 | 6.34 | 2968 | 5623 |
| CONSISTENCY4.10RR | 6 | 1.80 | 171 | 6.60 | 2951 | 5270 |
| WL363HQ | 6 | 1.98 | 171 | 6.30 | 2966 | 5826 |
| AMERISTAND407TQ | 6 | 1.79 | 170 | 6.59 | 2943 | 5223 |
| WL353LH | 6 | 1.83 | 170 | 6.38 | 2893 | 5263 |
| WL354HQ | 6 | 1.76 | 170 | 6.78 | 2871 | 4996 |
| KINGFISHER4020 | 6 | 1.96 | 169 | 6.49 | 2907 | 5627 |
| REBOUND6.0 | 6 | 1.75 | 169 | 6.62 | 2917 | 5055 |
| MagnumSalt | 6 | 1.90 | 168 | 6.47 | 2937 | 5540 |
| OACSUPERIOR | 6 | 1.87 | 168 | 6.44 | 2924 | 5409 |
| CW053093 | 6 | 1.81 | 168 | 6.62 | 2890 | 5142 |
| WL355RR | 6 | 1.75 | 165 | 6.55 | 2929 | 5125 |
| 6422Q | 6 | 1.92 | 164 | 6.72 | 2898 | 5519 |
| STARBUCK | 6 | 1.89 | 163 | 6.45 | 2898 | 5447 |
| HF2400 | 6 | 1.86 | 163 | 6.86 | 2892 | 5341 |
| 55V50 | 6 | 1.86 | 162 | 7.00 | 2858 | 5253 |
| PGI427 | 6 | 1.95 | 161 | 6.65 | 2886 | 5562 |
| DKA41-18RR | 6 | 1.70 | 161 | 6.64 | 2854 | 4830 |
| Magna551 | 6 | 1.87 | 160 | 6.68 | 2897 | 5366 |
| Magnum7-Wet | 6 | 1.93 | 160 | 6.84 | 2848 | 5422 |
| HF2420/Wet | 6 | 1.92 | 159 | 6.75 | 2881 | 5489 |
| HF2600 | 6 | 1.98 | 159 | 6.80 | 2861 | 5606 |
| PILLAR | 6 | 1.91 | 155 | 6.90 | 2813 | 5328 |
| 55V48 | 6 | 1.97 | 149 | 7.04 | 2795 | 5453 |
| Mean | | 1.91 | 163.0 | 6.65 | 2904.0 | 5460.5 |
| LSD (0.05) | | 0.13 | 13.7 | 0.43 | NS | 429.8 |
| CV % | | 5.9% | 7.4% | 5.7% | 3.7% | 7.0% |
| P-Value | | 0.000 | 0.003 | 0.002 | 0.231 | 0.000 |

TABLE 23

| HybriForce 3400 vs. CHECK | CUTS | % TA | % MT | % MA |
|---|---|---|---|---|
| DKA41-18RR | 6 | 12.8% | 1.9% | 14.2% |
| 54V46 | 23 | 12.3% | 1.5% | 13.6% |
| AttentionII | 23 | 11.5% | 4.0% | 15.3% |
| 55V12 | 15 | 9.6% | 1.6% | 11.1% |
| LABRADOR | 15 | 9.5% | 0.4% | 8.1% |
| 54H11 | 9 | 9.0% | 5.2% | 15.1% |
| 4A421 | 23 | 8.4% | 0.3% | 8.3% |
| WL357HQ | 23 | 8.4% | −0.7% | 7.6% |
| REBOUND6.0 | 21 | 5.5% | −0.3% | 4.6% |
| AMERISTAND407TQ | 28 | 5.2% | −0.2% | 4.0% |
| CONSISTENCY4.10RR | 14 | 5.2% | −1.3% | 2.6% |
| 55V48 | 44 | 4.7% | 2.2% | 5.9% |
| WL355RR | 14 | 4.6% | −1.5% | 2.3% |
| 6422Q | 21 | 4.4% | 0.0% | 3.0% |
| DKA43-13 | 16 | 3.9% | 0.1% | 3.3% |
| 55V50 | 6 | 3.7% | 2.8% | 6.4% |
| PGI557 | 15 | 3.5% | −1.7% | 0.9% |
| WL363HQ | 29 | 3.5% | −0.7% | 3.0% |
| ForageGold | 8 | 3.3% | 0.1% | 2.1% |
| WL343HQ | 29 | 3.3% | −0.5% | 2.4% |
| WL348AP | 14 | 3.1% | −0.9% | 1.7% |
| V-45RR | 8 | 2.9% | −0.6% | 0.2% |
| LIBERATORRR | 14 | 2.4% | −2.7% | −1.9% |
| WL354HQ | 14 | 2.1% | 1.9% | 2.5% |
| L-447HD | 8 | 2.0% | −1.8% | −0.7% |
| PILLAR | 13 | 1.5% | 3.3% | 4.1% |
| 54Q32 | 15 | 0.9% | −2.2% | −2.1% |
| MEAN | 468 | 5.4% | 0.4% | 5.1% |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A *Medicago sativa* seed designated as HybriForce-3400, wherein a sample of said seed has been deposited as ATCC Accession Number PTA-123758.

2. A plant, or a part thereof, produced by growing the seed of claim 1.

3. A pollen from the plant of claim 2.

4. An ovule from the plant of claim 2.

5. An alfalfa plant having all the physiological and morphological characteristics of the plant of claim 2.

6. A tissue culture of regenerable cells from the plant, or the part thereof, of claim 2.

7. The tissue culture of regenerable cells of claim 6, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

8. A protoplast produced from the tissue culture of claim 6.

9. The tissue culture of claim 6, wherein the culture is a callus culture.

10. An alfalfa plant regenerated from the tissue culture of claim 6, wherein the alfalfa plant has all of the physiological and morphological characteristics of a plant produced by growing a seed designated HybriForce-3400 and deposited under ATCC Accession No. PTA-123758.

11. A tissue culture of regenerable cells from the plant, or the part thereof, of claim 5.

12. The tissue culture of claim 11, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

13. A protoplast produced from the tissue culture of claim 11.

14. The tissue culture of claim 11, wherein the culture is a callus culture.

15. An alfalfa plant regenerated from the tissue culture of claim 11, wherein the plant has all of the physiological and morphological characteristics of a plant produced by growing a seed designated HybriForce-3400 and deposited under ATCC Accession No. PTA-123758.

16. A method for producing an alfalfa cultivar HybriForce-3400-derived alfalfa plant, comprising: (a) crossing HybriForce-3400 plants grown from HybriForce-3400 seed, representative seed of which has been deposited under ATCC Accession No: PTA-123758, with a second alfalfa plant to yield progeny alfalfa seed; and (b) growing the progeny seed to yield an alfalfa cultivar HybriForce-3400-derived alfalfa plant.

17. The method of claim 16, further comprising: (c) crossing the alfalfa cultivar HybriForce-3400-derived alfalfa plant of (b) with itself or a third alfalfa plant to yield a second alfalfa HybriForce-3400-derived alfalfa progeny seed; and (d) growing the second alfalfa progeny seed of (c) to yield a second alfalfa cultivar HybriForce-3400-derived alfalfa plant.

18. The method of claim 17, wherein (c) and (d) are repeated at least one time to generate an additional alfalfa cultivar HybriForce-3400-derived alfalfa plant.

19. A method of introducing a desired trait into alfalfa HybriForce-3400 comprising:
(a) crossing HybriForce-3400 plants grown from HybriForce-3400 seed, representative seed of which has been deposited under ATCC Accession No: PTA-123758, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates;
(b) selecting F1 progeny plants that have the desired trait to produce selected F1 progeny plants;
(c) crossing the selected progeny plants with the HybriForce-3400 plants to produce backcross progeny plants; (d) selecting for backcross progeny plants that have the desired trait and physiological and morphological characteristics of alfalfa variety HybriForce-3400 to produce selected backcross progeny plants; and
(e) repeating steps (c) and (d) three or more times in succession to produce selected fourth or higher backcross progeny plants that comprise the desired trait and all the physiological and morphological characteristics of alfalfa variety HybriForce-3400.

20. A plant produced by the method of claim 19, wherein the plant has the desired trait and all of the physiological and all morphological characteristics of said alfalfa variety HybriForce-3400.

21. A method for producing an alfalfa plant having an altered agronomic trait comprising introducing a polynucleotide into a HybriForce-3400 plant grown from HybriForce-3400 seed, representative seed of which has been deposited under ATCC Accession No: PTA-123758, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

22. An alfalfa plant produced by the method of claim 21, wherein the plant has the altered agronomic trait and all of the physiological and all morphological characteristics of said alfalfa variety HybriForce-3400.

23. A composition comprising a mixture of alfalfa seed, the mixture of alfalfa seed comprises between about 75% to about 95% of HybriForce-3400 seed, representative seed of HybriForce-3400 has been deposited under ATCC Accession No: PTA-123758.

* * * * *